United States Patent [19]

Ekholm et al.

[11] Patent Number: 4,652,127
[45] Date of Patent: Mar. 24, 1987

[54] APPARATUS FOR MEASURING CHARACTERISTICS OF LIQUID SAMPLES WHICH HAVE TO BE HEATED

[75] Inventors: Pertti Ekholm, Helsinki; Hannu Harjunmaa; Esko Kaukanen, both of Espoo; Osmo Suovaniemi, Helsinki, all of Finland

[73] Assignee: Labsystems Oy, Helsinki, Finland

[21] Appl. No.: 643,737

[22] Filed: Aug. 24, 1984

[30] Foreign Application Priority Data

Aug. 30, 1983 [FI] Finland ................................. 833076

[51] Int. Cl.⁴ .......................................... G01N 21/03
[52] U.S. Cl. ................................................ 356/246
[58] Field of Search ......................... 356/246; 350/533

[56] References Cited

FOREIGN PATENT DOCUMENTS 139645  8/1982  Japan ................................... 356/246
163845 10/1982  Japan ................................... 356/246

Primary Examiner—Vincent P. McGraw
Assistant Examiner—Matthew W. Koren
Attorney, Agent, or Firm—Hopgood, Calimafde, Kalil, Blaustein & Judlowe

[57] ABSTRACT

A photometer with controllable heating plates both above and below the set of sample cuvettes. The photometer is in particular used so that the upper plate is regulated to be warmer.

4 Claims, 2 Drawing Figures

APPARATUS FOR MEASURING CHARACTERISTICS OF LIQUID SAMPLES WHICH HAVE TO BE HEATED

The present invention concerns an apparatus, such as a photometer for instance, by which the optic characteristics of liquid samples placed in a set of cuvettes are measured. In particular, the invention concerns an apparatus in which the samples can be heated during measurement.

When liquid samples are being measured in optic analyzers, it is often necessary to heat the samples before or during the measurement.

As a rule, the heating has been arranged in that the set of cuvettes is immersed in a heatable aluminium body. One of the drawbacks encumbering this arrangement is that moisture condenses from the samples on the underside of the cover of the set of cuvettes provided with a cover.

It is also possible to circulate heated air around the set of cuvettes. However, a blower is required in this arrangement to ensure efficient operation.

It has now been understood that the heating may be arranged in a better way if both above and below the set of cuvettes is disposed a heating plate with a size at least equalling that of the set of cuvettes and the temperature of which can be controlled. It is possible to use, for such heating plates, printed circuit boards of which the conductor strips serve as heater resistances, or a continuous metal plate heated by heater resistances.

The advantage of the apparatus of the invention is, above all, uniform and controllable heating. It is moreover possible, in the apparatus, to prevent condensation on the cover of the set of cuvettes by regulating the upper heating plate to have a temperature higher than that of the lower heating plate. Control of the heating becomes particularly simple when printed circuit boards are used.

The arrangement interferes in no way with the moving of the set of cuvettes and the heating plates relative to each other; such moving may be necessary in order to subject different samples to measurement.

Certain advantageous embodiments of the invention are more closely illustrated by the aid of Drawings 1 and 2.

Figure 1:
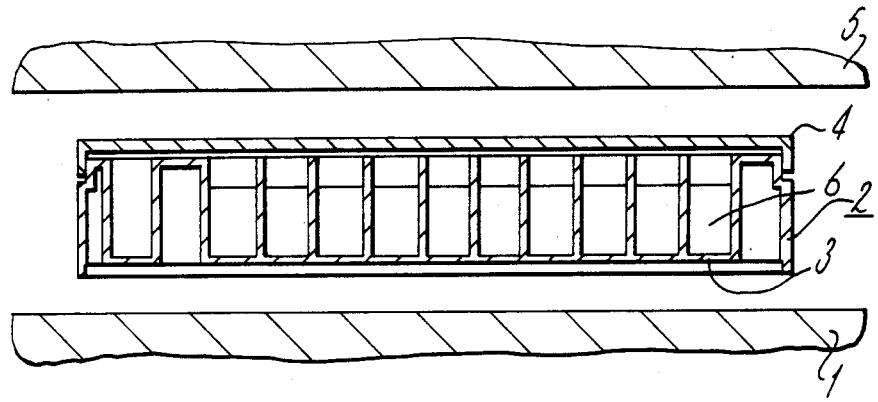
FIG. 1 is a side elevation of the disclosed apparatus.

The apparatus depicted in FIG. 1 has two hot plates 1 and 5, and between them a set of cuvettes 2 with a cover. Between the lower hot plate 1 and the bottom 3 of the set of cuvettes is defined an air space which may have a height e.g. between 0.1 and 10 mm. An air space with the same order of magnitude is likewise defined between the cover 4 of the set of cuvettes and the upper hot plate 5. The set of cuvettes contains the liquid sample 6.

The heat is transported from the hot plates to the set of cuvettes mainly by radiation. The desired temperature may be for instance 37° C. At this temperature, the maximum intensity of thermal radiation is at a wavelength about 10 nm, at which all those plastics of which sets of cuvettes are usually made are opaque. As a result, the thermal radiation emitted by the lower hot plate is absorbed in the bottom of the set of cuvettes and that emitted by the upper hot plate, in the cover. The heat is conducted to the sample mainly through the bottom of the set of cuvettes because the thermal contact between the cover and the set of cuvettes is poor.

Figure 2:
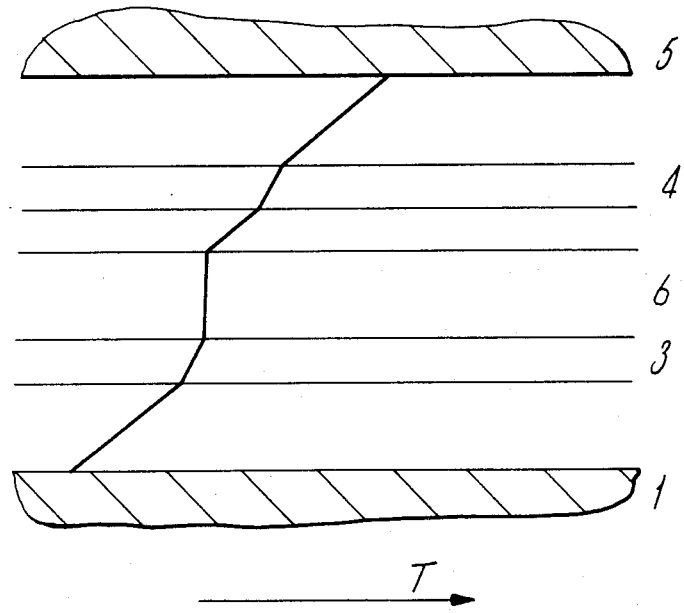
FIG. 2 is a schematic representation of temperature distribution in the apparatus.

When equilibrium has been reached, the temperature distribution schematically shown in FIG. 2 prevails in the system. Since the heat is mainly transported into the sample from below, a convection flow is set up in each cuvette, which keeps the sample at uniform temperature. The temperature of the underside of the cover of the set of cuvettes is higher than that of the top surface of the sample all the time. For this reason no moisture will condense on the underside of the cover even if the air space between it and the sample surface should become saturated with vapour.

The measuring station where for instance a photometric measurement is carried out vertically with the cover of the set of cuvettes in place may be located in a part of the apparatus outside the hot plates, or fixedly connected with the hot plates so that the light transmitter has been accommodated in one of the hot plates and the detector in the other. It is also possible to dispose a measuring head, moving at right angles against the direction of movement of the set of cuvettes, in slots provided in the hot plates at right angles against the direction of movement of the set of cuvettes.

We claim:

1. In an apparatus for measuring the optic characteristics of liquid samples contained within a set of cuvettes with a lower heating surface and an upper heating surface, a means for gradiently heating said cuvettes and uniformly heating samples within said cuvettes comprising a first heat source disposed at a distance of from 0.1 to 10 mm below said cuvettes and horizontally thereto and a second heat source disposed at a distance of from 0.1 to 10 mm above said cuvettes and horizontally thereto and wherein said first heat source is maintained at lower temperature than said second heat source such that the lower heating surface of said cuvette is maintained at a temperature lower than the upper heating surface of said cuvette and said sample is uniformly heated.

2. The apparatus of claim 1 wherein the first and second heat source are printed circuit boards bearing conductor strips wherein said conductor strips serve as heater resistances.

3. In a method for measuring the optic characteristics of liquid samples contained within a set of cuvettes with an upper heating surface and a lower heating surface, the improvement comprising a method for gradiently heating said cuvettes and uniformly heating said samples comprising (a) exposing the lower heating surface of said cuvettes to a heating means disposed and 0.1 to 10 mm below said cuvettes and horizontally thereto, and (b) exposing the upper heating surface of said cuvettes to a heating means disposed and 0.1 to 10 mm above said cuvettes and horizontally thereto, (c) maintaining the lower surface heating means at a temperature below that of said upper surface heating means, (d) maintaining the temperature of the lower heating surface of said cuvettes at a temperature lower than the upper heating surface, and (e) uniformly heating the liquid samples of said cuvettes.

4. The method of claim 3 further comprising maintaining the upper surface heating means at a temperature such that the top surface of said cuvette will be maintained at a temperature above the condensation point of said liquid samples.

* * * * *